(12) United States Patent
McNevin et al.

(10) Patent No.: US 11,292,810 B2
(45) Date of Patent: Apr. 5, 2022

(54) INCLUSION COMPLEXES OF AN HCV NS5B INHIBITOR AND USES THEREOF

(71) Applicant: Merck Sharp & Dohme Corp., Rahway, NJ (US)

(72) Inventors: Michael J. McNevin, Doylestown, PA (US); Alfred Lee, Robbinsville, NJ (US); Jason T. Ash, Green Brook, NJ (US); Itzia Arroyo, Union, NJ (US); Binfeng Xia, Chester Springs, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 276 days.

(21) Appl. No.: 16/710,724

(22) Filed: Dec. 11, 2019

(65) Prior Publication Data

US 2020/0190131 A1    Jun. 18, 2020

Related U.S. Application Data

(60) Provisional application No. 62/781,298, filed on Dec. 18, 2018.

(51) Int. Cl.
| | | |
|---|---|---|
| A01N 43/04 | (2006.01) | |
| A61K 31/70 | (2006.01) | |
| C07H 19/10 | (2006.01) | |
| C07C 53/126 | (2006.01) | |

(52) U.S. Cl.
CPC .......... *C07H 19/10* (2013.01); *C07C 53/126* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 9,061,041 B2 | 6/2015 | Girijavallabhan et al. | |
| 2017/0226146 A1 | 8/2017 | Chung et al. | |
| 2017/0275327 A1 | 9/2017 | Edwards et al. | |
| 2017/0334926 A1 | 11/2017 | DiRocco et al. | |
| 2018/0011954 A1 | 1/2018 | Micks et al. | |

FOREIGN PATENT DOCUMENTS

| | | |
|---|---|---|
| WO | WO2013177219 A1 | 11/2013 |
| WO | 2014058801 A1 | 4/2014 |
| WO | 2016064797 A1 | 4/2016 |

OTHER PUBLICATIONS

Severino et al. Current State-of-Art and New Trends on Lipid Nanoparticles (SLN and NLC) for Oral Drug Delivery. J Drug Deliv. 2012;2012:750891.doi: 10.1155/2012/750891. Epub Nov. 24, 2011. PMID: 22175030; PMCID: PMC3228282.*
Lembo et al. Expert Opinion on Drug Delivery (2018), vol. 15, pp. 93-114.*
Manjunath et al. Methods Find Exp Clin Pharmacol (2005), vol. 27, pp. 1-20.*

* cited by examiner

*Primary Examiner* — Patrick T Lewis
(74) *Attorney, Agent, or Firm* — Jeffrey P. Bergman; Catherine D. Fitch

(57) ABSTRACT

The present invention relates to novel Inclusion Complexes of Compound A, compositions comprising an Inclusion Complex of Compound A, and methods of using the Inclusion Complexes of Compound A for preparing compositions useful for treating or preventing HCV infection in a patient, wherein Compound A has the structure:

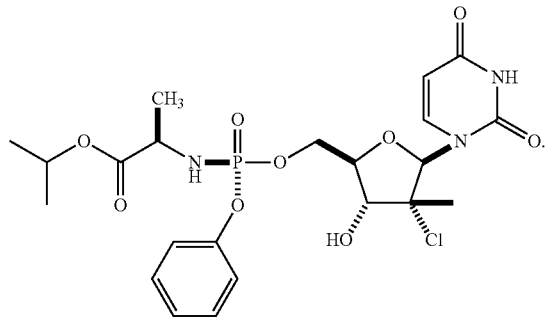

17 Claims, No Drawings

INCLUSION COMPLEXES OF AN HCV NS5B INHIBITOR AND USES THEREOF

FIELD OF THE INVENTION

The present invention relates to novel Inclusion Complexes of an HCV NS5B Polymerase inhibitor (Compound A), compositions comprising an Inclusion Complex of Compound A, and methods of using an Inclusion Complex of Compound A for preparing compositions useful for treating or preventing HCV infection in a patient.

BACKGROUND OF THE INVENTION

Various substituted nucleoside compounds are known inhibitors of the HCV NS5B protease enzyme. Inhibition of HCV NS5B polymerase prevents formation of the double-stranded HCV RNA and therefore constitutes an attractive approach to the development of HCV-specific antiviral therapies. Included in these nucleosides are nucleoside phosphoramidate compounds, such as (R)-isopropyl 2-(((R)-(((2R,3R,4R,5R)-4-chloro-5-(2,4-dioxo-3,4-dihydropyrimidin-1(2H)-yl)-3-hydroxy-4-methyltetrahydrofuran-2-yl)methoxy)(phenoxy)phosphoryl)amino)propanoate, hereinafter referred to as Compound A. Compound A is a known inhibitor of HCV NS5B polymerase and is useful for the treatment of HCV infection. The structure of Compound A is as follows:

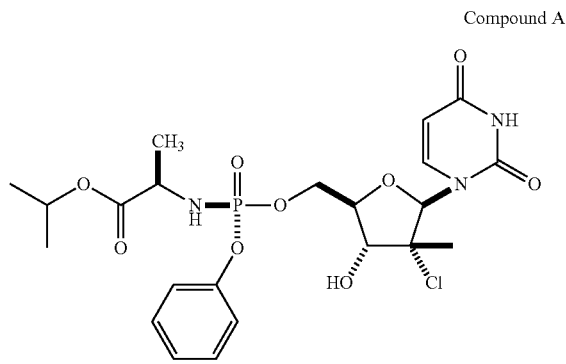 [SMILES: CC(C)OC(=O)[C@@H](C)N[P@@](=O)(OC[C@H]1O[C@@H](n2ccc(=O)[nH]c2=O)[C@](C)(Cl)[C@@H]1O)Oc1ccccc1]

Compound A

Compound A is described, for example, in International Patent Publication Nos. WO 2013/177219 and WO 2014/058801.

International Patent Publication Nos. WO 2013/177219 and WO 2014/058801 disclose methods that can be used to prepare Compound A and related nucleoside HCV NS5B inhibitors. These methods are practical routes for the preparation of Compound A and related nucleoside phosphoramidate compounds.

SUMMARY OF THE INVENTION

In one aspect, the present invention provides Inclusion Complexes (the "Inclusion Complexes of Compound A") comprising (a) the compound having the structure:

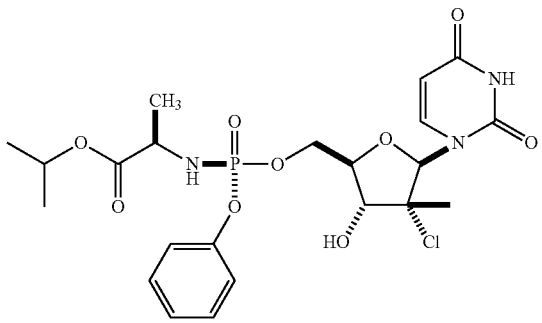 [SMILES: CC(C)OC(=O)[C@@H](C)N[P@@](=O)(OC[C@H]1O[C@@H](n2ccc(=O)[nH]c2=O)[C@](C)(Cl)[C@@H]1O)Oc1ccccc1]

Compound A and (b) at least one long-chain fatty acid.

In another aspect, the present invention provides pharmaceutical compositions comprising an Inclusion Complex of Compound A.

In another aspect, the present invention provides a method for treating HCV in a patient, said method comprising administering to said patient, an Inclusion Complex of Compound A.

The Inclusion Complexes of Compound A can be useful, for example, for inhibiting HCV viral replication or replicon activity, for treating or preventing HCV infection in a patient, and for preparing amorphous dosage forms. Without being bound by any specific theory, it is believed that Inclusion Complexes of Compound A inhibit HCV viral replication by inhibiting HCV NS5B polymerase.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to novel Inclusion Complexes of Compound A, compositions comprising an Inclusion Complex of Compound A, and methods of using an Inclusion Complex of Compound A for treating or preventing HCV infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "dosage form" refers to a pharmaceutical product comprising an Inclusion Complex of Compound A, wherein the pharmaceutical product is in the form suitable for administration. The dosage form comprises a mixture of active drug component(s) and nondrug component(s) (excipient(s)), along with other non-reusable material that may not be considered either ingredient or packaging (such as a capsule shell, for example). The term "dosage form" also refers to a chemical formulation comprising an Inclusion Complex of Compound A and any blends involved, without considering its ultimate configuration as a consumable product such as a tablet or capsule. Depending on the method/route of administration, a dosage forms may exist in several types. These include, but are not limited to, liquid, solid, and semisolid dosage forms. Non-limiting dosage forms include pills, tablets, capsules, suspensions, drinks or syrups. A dosage form can be administered various ways, including orally and intravenously.

The term "effective amount" as used herein, refers to an amount of an Inclusion Complex of Compound A and/or an additional therapeutic agent, or a composition thereof that is effective in inhibiting HCV replication and preferably in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective.

The term "preventing," as used herein with respect to an HCV viral infection or HCV-virus related disorder, refers to reducing the likelihood of HCV infection.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization, and the like), in sufficient purity to be characterizable by standard analytical techniques described herein or well-known to the skilled artisan.

It should also be noted that any carbon as well as any heteroatom with unsatisfied valences in the text, schemes, examples and tables herein is assumed to have the sufficient number of hydrogen atom(s) to satisfy the valences.

As used herein, the term "composition" is intended to encompass a product comprising the specified ingredients in the specified amounts, as well as any product which results from combination of the specified ingredients in the specified amounts.

The term "long-chain fatty acid" refers to a carboxylic acid having a long aliphatic chain, wherein the long aliphatic chain is a: (a) straight or branched, and (b) saturated or unsaturated hydrocarbon having from about 14 to about 20 carbon atoms. Illustrative examples of long-chain fatty acids include, but are not limited to myristic acid, palmitic acid, stearic acid, and arachadic acid. In one embodiment the long-chain fatty acid is palmitic acid. In another embodiment the long-chain fatty acid is stearic acid.

All stereoisomers (for example, geometric isomers, optical isomers and the like) of the present compounds (including those of the salts, solvates, hydrates and esters of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention.

The Inclusion Complexes of Compound A

The present invention provides an inclusion complex comprising: (a) the compound having the structure:

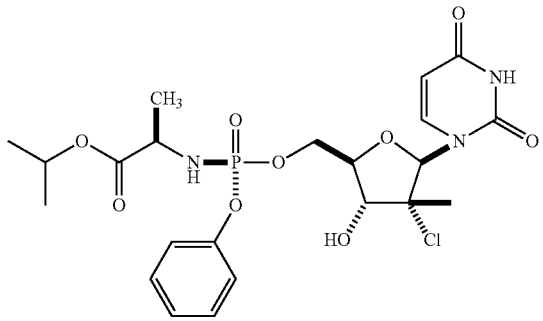 [SMILES: CC(C)OC(=O)[C@@H](C)N[P@@](=O)(OC[C@H]1O[C@@H](n2ccc(=O)[nH]c2=O)[C@](C)(Cl)[C@@H]1O)Oc1ccccc1]

or a pharmaceutically acceptable salt thereof, and (b) at least one long-chain fatty acid.

In one embodiment, the long-chain fatty acid is palmitic acid.

In another embodiment, the long-chain fatty acid is stearic acid.

In another embodiment, the long-chain fatty acid is myristic acid.

In still another embodiment, the long-chain fatty acid is arachadic acid.

In another embodiment, the long-chain fatty acid is a mixture of palmitic acid and stearic acid.

In one embodiment, the inclusion complex has a stoichiometry of (a) to (b) of from 20:1 to 1:1.

In another embodiment, the inclusion complex has a stoichiometry of (a) to (b) of from 5:1 to 1:1.

In another embodiment, the inclusion complex has a stoichiometry of (a) to (b) of about 1:1.

In one embodiment, the Inclusion Complex of Compound A is in amorphous form.

In one embodiment, the Inclusion Complex of Compound A comprises: (a) Compound A, or a pharmaceutically acceptable salt thereof, and (b) palmitic acid, and is characterized by an X-ray powder diffraction pattern having peaks at 2-theta values, when measured using Cu $K_\alpha$ radiation, of about 6.57, 6,87, 17.93, and 21.03 degrees.

In another embodiment, the Inclusion Complex of Compound A comprises: (a) Compound A, or a pharmaceutically acceptable salt thereof, and (b) stearic acid, and is characterized by an X-ray powder diffraction pattern having peaks at 2-theta values, when measured using Cu $K_\alpha$ radiation, of about 6.57, 6.90, 17.90, and 20.98 degrees.

In another embodiment, the Inclusion Complex of Compound A comprises: (a) Compound A, or a pharmaceutically acceptable salt thereof; (b) stearic acid; and (c) palmitic acid, and is characterized by an X-ray powder diffraction pattern having peaks at 2-theta values, when measured using Cu $K_\alpha$ radiation, of about 6.55, 15.62, 17.94, and 19.17 degrees.

In one embodiment, the Inclusion Complex of Compound A comprises: (a) Compound A, or a pharmaceutically acceptable salt thereof, and (b) palmitic acid, and is characterized by a DSC thermogram having an endothermic transition at about 132 degrees centrigrade.

In another embodiment, the Inclusion Complex of Compound A comprises: (a) Compound A, or a pharmaceutically acceptable salt thereof, and (b) stearic acid, and is characterized by a DSC thermogram having an endothermic transition at about 131 degrees centrigrade.

In another embodiment, the Inclusion Complex of Compound A comprises: (a) Compound A, or a pharmaceutically acceptable salt thereof; (b) stearic acid; and (c) palmitic acid, and is characterized by a DSC thermogram having an endothermic transition at about 131 degrees centrigrade.

In one embodiment, the Inclusion Complex of Compound A comprises: (a) Compound A, or a pharmaceutically acceptable salt thereof, and (b) palmitic acid, and is characterized by a solid state carbon-13 NMR spectrum having isotropic chemical shifts at 14.85, 21.74, 22.56, 26.04, 29.14, 30.63, 31.14, 32.43, 33.56, 37.07, 49.41, 49.99, 62.99, 68.62, 69.78, 72.29, 77.00, 78.20, 80.53, 93.56, 102.11, 103.87, 119.96, 120.78, 123.72, 125.13, 129.78, 133.94, 141.64, 150.46, 151.22, 152.12, 167.11, 173.97, 181.75, and 183.24 ppm.

In another embodiment, the Inclusion Complex of Compound A comprises: (a) Compound A, or a pharmaceutically acceptable salt thereof, and (b) stearic acid, and is characterized by a solid state carbon-13 NMR spectrum having isotropic chemical shifts at 15.54, 20.31, 21.7023, 22.48, 26.14, 27.20, 29.29, 30.62, 31.16, 34.03, 37.18, 49.36, 50.11, 63.25, 68.68, 69.92, 72.27, 77.27, 78.15, 80.52, 92.65, 93.52, 102.11, 103.90, 120.00, 120.60, 123.83, 125.12, 129.69, 133.82, 141.59, 150.42, 151.15, 152.16, 167.04, 174.15, 181.94, and 183.46 ppm.

In another embodiment, the Inclusion Complex of Compound A comprises: (a) Compound A, or a pharmaceutically acceptable salt thereof; (b) stearic acid; and (c) palmitic acid, and is characterized by a solid state carbon-13 NMR spectrum having isotropic chemical shifts at 14.98, 20.45, 21.78, 22.49, 26.13, 29.29, 30.65, 31.15, 32.52, 33.58, 37.11, 49.38, 50.05, 63.14, 68.63, 69.85, 72.28, 77.09, 78.20, 80.54, 93.53, 102.12, 103.88, 119.99, 120.76, 123.84, 125.15, 129.75, 133.85, 141.59, 150.46, 151.20, 152.16, 167.08, 174.05, 181.86, and 183.36 ppm.

In one aspect, the present invention relates to processes for preparing Inclusion Complexes of Compound A. Inclusion Complexes of Compound A are prepared by combining Compound A with at least one long-chain fatty acid in an organic solvent, or water, or mixtures of water and water miscible organic solvents, applying any suitable technique to induce crystallization, and isolating the desired Inclusion Complex. The Inclusion Complexes of Compound A may be prepared from Compound A using methods known to one skilled in the art of organic synthesis. Methods useful for making the Inclusion Complexes of Compound A are set forth herein. Alternative synthetic pathways and analogous structures will be apparent to those skilled in the art of organic synthesis.

Removing and/or separating any undesired material or impurities may be performed by purification, filtering, washing, precipitation or similar techniques. Separation, for example, can be conducted using known solid-liquid separation techniques. Filtering procedures known to those skilled in the art can also be used in the present process. The filtrations can be performed, amongst other methods, by centrifugation, or using Buchner style filter, Rosenmund filter or plates, or frame press. In one embodiment, in-line filtration or safety filtration may be advantageously used in the processes disclosed above, in order to increase the purity of the resulting inclusion complexic form. Additionally, filtering agents such as silica gel, Arbocel®, dicalite diatomite, or the like, may also be used to purify the crystals of interest.

Crystals obtained may be also dried, and such drying process may optionally be used in the different crystallization processes, if more than one crystallization process is applied. Drying procedures useful in the present methods include, but are not limited to, such as heating, applying vacuum, circulating air or gas, adding a desiccant, freeze-drying, spray-drying, evaporating, or the like, or any combination thereof.

Breaking up the large crystalline particles or aggregates of particles after formation of an Inclusion Complex of Compound A may additionally be performed in order to obtain a desired and homogeneous particle size. Accordingly, the crystals of an Inclusion Complex of Compound A can be optionally milled after undergoing conversion. Milling or grinding refers to physically breaking up the large particles or aggregates of particles using methods and apparatus well known in the art for particle size reduction of powders. Resulting particle sizes may range from millimeters to nanometers, yielding i.e. nanocrystals, microcrystals.

The yield of the preparation process of the Inclusion Complexes of Compound A may be 10% or more. In one embodiment, the yield is from about 40% to about 100%. In one embodiment, the yield is from about 75% to about 100%.

In one embodiment, the Inclusion Complexes of the present invention have a purity greater than 90 percent. In another embodiment, the Inclusion Complexes of the present invention have a purity greater than 95 percent. In still another embodiment, the Inclusion Complexes of the present invention have a purity greater than 99 percent.

In one embodiment, the Inclusion Complexes of Compound A are in substantially purified form.

Other embodiments of the present invention include the following:

(a) A pharmaceutical composition comprising an effective amount of an Inclusion Complex of Compound A, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5A inhibitors.

(d) A pharmaceutical combination that comprises: (i) an Inclusion Complex of Compound A and (ii) a second therapeutic agent selected from the group consisting of HCV antiviral agents, immunomodulators, and anti-infective agents; wherein the amorphous Compound A and the second therapeutic agent are each employed in an amount that renders the combination effective for inhibiting HCV replication, or for treating HCV infection and/or reducing the likelihood or severity of symptoms of HCV infection.

(e) The combination of (d), wherein the second therapeutic agent is an antiviral agent selected from the group consisting of HCV protease inhibitors and HCV NS5A inhibitors.

(f) A method of inhibiting HCV replication in a subject in need thereof which comprises administering to the subject an effective amount of an Inclusion Complex of Compound A.

(g) A method of treating HCV infection and/or reducing the likelihood or severity of symptoms of HCV infection in a subject in need thereof which comprises administering to the subject an effective amount of an Inclusion Complex of Compound A.

(h) The method of (g), wherein the Inclusion Complex of Compound A is administered in combination with an effective amount of at least one second therapeutic agent selected from the group consisting of HCV antiviral agents, immunomodulators, and anti-infective agents.

(i) The method of (h), wherein the second therapeutic agent is an antiviral agent selected from the group consisting of HCV protease inhibitors and HCV NS5A inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

The present invention also includes Inclusion Complexes of Compound A for use (i) in, (ii) as a medicament for, or (iii) in the preparation of a medicament for: (a) medicine; (b) inhibiting HCV replication or (c) treating HCV infection and/or reducing the likelihood or severity of symptoms of HCV infection. In these uses, the Inclusion Complex of Compound A can optionally be employed in combination with one or more additional therapeutic agents selected from HCV antiviral agents, anti-infective agents, and immunomodulators.

It is further to be understood that the embodiments of compositions and methods provided as (a) through (k) above are understood to include all embodiments of the compounds, including such embodiments as result from combinations of embodiments.

Non-limiting examples of the Inclusion Complexes of Compound A are described in the Examples below.

Uses of Inclusion Complexes of Compound A

Treatment or Prevention of a Flaviviridae Virus

The Inclusion Complexes of Compound A can be useful for treating or preventing a viral infection caused by the Flaviviridae family of viruses. In one embodiment, the Flaviviridae infection being treated is hepatitis C virus infection.

Treatment or Prevention of HCV Infection

Inclusion Complexes of Compound A are useful in the inhibition of HCV (e.g., HCV NS5B polymerase), the treatment of HCV infection and/or reduction of the likelihood or severity of symptoms of HCV infection and the inhibition of HCV viral replication and/or HCV viral production in a cell-based system. For example, Inclusion Complexes of Compound A are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of an Inclusion Complex of Compound A. In a specific embodiment, the amount administered is effective to treat or prevent infection by HCV in the patient. In another specific embodiment, the amount administered is effective to inhibit HCV viral replication and/or viral production in the patient.

The Inclusion Complexes of Compound A are also useful in the preparation and execution of screening assays for antiviral compounds. For example the Inclusion Complexes of Compound A can be useful for identifying resistant HCV replicon cell lines harboring mutations within HCV NS5B polymerase, which are useful screening tools for more powerful antiviral compounds. Furthermore, the Inclusion Complexes of Compound A can be useful in establishing or determining the binding site of other antivirals to the HCV replicase.

Compositions and Administration

When administered to a patient, an Inclusion Complex of Compound A can be administered as a component of a composition that comprises a pharmaceutically acceptable carrier or vehicle. The present invention provides pharmaceutical compositions comprising an effective amount of an Inclusion Complex of Compound A and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Inclusion Complex of Compound A is administered orally.

In another embodiment, the Inclusion Complex of Compound A is administered intravenously.

In another embodiment, the Inclusion Complex of Compound A is administered topically.

In still another embodiment, the Inclusion Complex of Compound A is administered sublingually.

In one embodiment, a pharmaceutical preparation comprising an Inclusion Complex of Compound A is in unit dosage form. In such form, the preparation is subdivided into unit doses containing effective amounts of the active components.

Compositions can be prepared using techniques such as conventional mixing, granulating or coating methods; and by using solid dispersion based upon the guidance provided herein. In one embodiment, the present compositions can contain from about 0.1% to about 99% of an Inclusion Complex of Compound A by weight or volume. In various embodiments, the present compositions can contain, in one embodiment, from about 1% to about 70% or from about 5% to about 60% of an Inclusion Complex of Compound A by weight or volume.

The quantity of an Inclusion Complex of Compound A in a unit dose of preparation may be varied or adjusted from about 1 mg to about 2500 mg. In various embodiments, the quantity is from about 10 mg to about 1000 mg, 1 mg to about 500 mg, 1 mg to about 100 mg, and 1 mg to about 100 mg.

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Inclusion Complex of Compound A and the other agent(s) can be administered simultaneously (i.e., in the same composition or in separate compositions one right after the other) or sequentially. This is particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms can therefore be advantageous.

Generally, a total daily dosage of an Inclusion Complex of Compound A alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of an Inclusion Complex of Compound A will be regulated according to the judgment of the attending clinician considering such factors as age, condition and size of the patient as well as severity of the symptoms being treated. Generally, a total daily dosage of an Inclusion Complex of Compound A range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) an Inclusion Complex of Compound A; (ii) one or more additional therapeutic agents that are not Inclusion Complexes of Compound A; and (iii) a pharmaceutically acceptable carrier, wherein the amounts in the composition are together effective to treat HCV infection.

In one embodiment, the present invention provides compositions comprising an Inclusion Complex of Compound A and a pharmaceutically acceptable carrier.

In another embodiment, the present invention provides compositions comprising an Inclusion Complex of Compound A, a pharmaceutically acceptable carrier, and a second therapeutic agent selected from the group consisting of HCV antiviral agents, immunomodulators, and anti-infective agents.

In another embodiment, the present invention provides compositions comprising an Inclusion Complex of Compound A, a pharmaceutically acceptable carrier, and two additional therapeutic agents, each of which are independently selected from the group consisting of HCV antiviral agents, immunomodulators, and anti-infective agents.

Combination Therapy

In another embodiment, the present methods for treating or preventing HCV infection can further comprise the administration of one or more additional therapeutic agents that are other than the Inclusion Complexes of Compound A.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) an Inclusion Complex of Compound A, or a pharmaceutically acceptable salt thereof, and (ii) at least one additional therapeutic agent that is other than an Inclusion Complex of Compound A, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, the Inclusion Complex of Compound A and an additional therapeutic agent may be present in fixed amounts (dosage amounts) in a single dosage unit (e.g., a capsule, a tablet and the like).

In one embodiment, the Inclusion Complex of Compound A is administered during a time when the additional therapeutic agent(s) exert their prophylactic or therapeutic effect, or vice versa.

In another embodiment, the Inclusion Complex of Compound A and the additional therapeutic agent(s) are administered in doses commonly employed when such agents are used as monotherapy for treating a viral infection.

In another embodiment, the Inclusion Complex of Compound A and the additional therapeutic agent(s) are administered in doses lower than the doses commonly employed when such agents are used as monotherapy for treating a viral infection.

In still another embodiment, the Inclusion Complex of Compound A and the additional therapeutic agent(s) act synergistically and are administered in doses lower than the doses commonly employed when such agents are used as monotherapy for treating a viral infection.

In one embodiment, the Inclusion Complex of Compound A and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The Inclusion Complex of Compound A and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of the Inclusion Complex of Compound A and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5A inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), R7128 (Roche/Pharmasset), PF-868554/filibuvir (Pfizer), VCH-759 (ViroChem Pharma), HCV-796 (Wyeth/ViroPharma), IDX-184 (Idenix), IDX-375 (Idenix), NM-283 (Idenix/Novartis), R-1626 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH222 (ViroChem), VCH916 (ViroChem), VCH716 (ViroChem), GSK-71185 (Glaxo SmithKline), ANA598 (Anadys), GSK-625433 (Glaxo SmithKline), XTL-2125 (XTL Biopharmaceuticals), sofosbuvir (Gilead), uprifosbuvir (Merck) and those disclosed in Ni et al., *Current Opinion in Drug Discovery and Development*, 7 (4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), IFN-α-2b-XL (Flamel Technologies), and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124148.

Additional HCV protease inhibitors useful in the present compositions and methods include, but are not limited to, Grazoprevir (Merck), SCH503034 (Boceprevir, Merck), SCH900518 (Schering-Plough), VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott), TMC-435350 (Medivir), ITMN-191/R7227 (InterMune/Roche), EA-058 (Abbott/Enanta), EA-063 (Abbott/Enanta), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, those disclosed in Landro et al., *Biochemistry*, 36 (31):9340-9348 (1997); Ingallinella et al., *Biochemistry*, 37 (25):8906-8914 (1998); Llinàs-Brunet et al., *Bioorg Med Chem Lett*, 8 (13):1713-1718 (1998); Martin et al., *Biochemistry*, 37 (33):11459-11468 (1998); Dimasi et al., *J Virol*, 71 (10):7461-7469 (1997); Martin et al., *Protein Eng*, 10 (5): 607-614 (1997); Elzouki et al., *J Hepat*, 27 (1):42-48 (1997); *BioWorld Today*, 9 (217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), BMS-790052 (Bristol-Myers Squibb, see Gao et al., *Nature*, 465:96-100 (2010)), viramidine, A-831 (Arrow Therapeutics); an antisense agent or a therapeutic vaccine.

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful in the useful in the present compositions and methods include, but are not limited to, AZD2836 (Astra Zeneca) and ACH-806 (Achillon Pharmaceuticals, New Haven, Conn.).

HCV replicase inhibitors useful in the useful in the present compositions and methods include, but are not limited to, those disclosed in U.S. Patent Publication No. US20090081636.

Therapeutic vaccines useful in the present compositions and methods include, but are not limited to, Inclusion Complex41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPROTM (Pevion Biotect), HCV/MF59 (Chiron/Novartis) and Civacir (NABI).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (Inclusion ComplexN Pharmaceuticals, Costa Mesa, Calif.); Humax (Genmab), ITX-2155 (Ithrex/Novartis), PRO 206 (Progenics), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

In one embodiment, when the additional therapeutic agent is INTRON-A interferon alpha 2b, which is administered by subcutaneous injection at 3 MIU (12 mcg)/0.5 mL/TIW for 24 weeks or 48 weeks for first time treatment.

In another embodiment, when the additional therapeutic agent is PEG-INTRON interferon alpha 2b pegylated (commercially available from Merck), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3 MIU (11.1 mcg/mL)/TIW for at least 48 to 52 weeks, or alternatively 6 MIU/TIW for 12 weeks followed by 3 MIU/TIW for 36 weeks.

In still another embodiment, when the additional therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Merck, or COPEGUS ribavirin from Hoffmann-La Roche), this agent is administered at a daily dosage of from about 600 to about 1400 mg/day for at least 24 weeks.

In one embodiment, the Inclusion Complex of Compound A is administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, the Inclusion Complex of Compound A is administered with one or more additional therapeutic agents selected from an HCV protease inhibitor, an HCV polymerase inhibitor, an HCV replication inhibitor, a nucleoside, an interferon, a pegylated interferon and ribavirin. The combination therapies can include any combination of these additional therapeutic agents.

In another embodiment, the Inclusion Complex of Compound A is administered with one additional therapeutic agent selected from an HCV protease inhibitor, an interferon, a pegylated interferon and ribavirin.

In still another embodiment, the Inclusion Complex of Compound A is administered with two additional therapeutic agents selected from an HCV protease inhibitor, an HCV replication inhibitor, a nucleoside, an interferon, a pegylated interferon and ribavirin.

In another embodiment, the Inclusion Complex of Compound A is administered with an HCV protease inhibitor and ribavirin. In another specific embodiment, the Inclusion Complex of Compound A is administered with a pegylated interferon and ribavirin.

In another embodiment, the Inclusion Complex of Compound A is administered with three additional therapeutic agents selected from an HCV protease inhibitor, an HCV replication inhibitor, a nucleoside, an interferon, a pegylated interferon and ribavirin.

In one embodiment, the Inclusion Complex of Compound A is administered with one or more additional therapeutic agents selected from an HCV polymerase inhibitor, a viral protease inhibitor, an interferon, and a viral replication inhibitor. In another embodiment, the Inclusion Complex of Compound A is administered with one or more additional therapeutic agents selected from an HCV polymerase inhibitor, a viral protease inhibitor, an interferon, and a viral replication inhibitor. In another embodiment, the Inclusion Complex of Compound A is administered with one or more additional therapeutic agents selected from an HCV polymerase inhibitor, a viral protease inhibitor, an interferon, and ribavirin.

In another embodiment, the Inclusion Complex of Compound A is administered with one additional therapeutic agent selected from an HCV polymerase inhibitor, a viral protease inhibitor, an interferon, and a viral replication inhibitor. In another embodiment, the Inclusion Complex of Compound A is administered with ribavirin.

In another embodiment, the Inclusion Complex of Compound A is administered with two additional therapeutic agents selected from an HCV polymerase inhibitor, a viral protease inhibitor, an interferon, and a viral replication inhibitor.

In yet another embodiment, the Inclusion Complex of Compound A is administered with ribavirin, interferon and another therapeutic agent.

In another embodiment, the Inclusion Complex of Compound A is administered with ribavirin, interferon and another therapeutic agent, wherein the additional therapeutic agent is selected from an HCV polymerase inhibitor, a viral protease inhibitor, and a viral replication inhibitor.

In still another embodiment, the Inclusion Complex of Compound A is administered with ribavirin, interferon and a viral protease inhibitor.

In another embodiment, the Inclusion Complex of Compound A is administered with ribavirin, interferon and an HCV protease inhibitor.

In another embodiment, the Inclusion Complex of Compound A is administered with ribavirin, interferon and boceprevir or telaprevir.

In a further embodiment, the Inclusion Complex of Compound A is administered with ribavirin, interferon and an HCV polymerase inhibitor.

In another embodiment, the Inclusion Complex of Compound A is administered with pegylated-interferon alpha and ribavirin.

Kits

In one aspect, the present invention provides a kit comprising a therapeutically effective amount of an Inclusion Complex of Compound A, or a pharmaceutically acceptable salt, solvate or ester of said compound and a pharmaceutically acceptable carrier, vehicle or diluent.

In another aspect the present invention provides a kit comprising an amount of an Inclusion Complex of Compound A, and an amount of at least one additional therapeutic agent listed above, wherein the amounts of the two or more active ingredients result in a desired therapeutic effect. In one embodiment, the Inclusion Complex of Compound A and the one or more additional therapeutic agents are provided in the same container. In one embodiment, the Inclusion Complex of Compound A and the one or more additional therapeutic agents are provided in separate containers.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm downfield from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% $CH_3CN$, 5 minutes—95% $CH_3CN$, 5-7 minutes—95% $CH_3CN$, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

The X-ray powder diffraction patterns disclosed herein were generated on a Philips Analytical X'Pert PRO X-ray Diffraction System with PW3040/60 console. A PW3373/00 ceramic Cu LEF X-ray tube K-Alpha radiation was used as the source.

Solid-state carbon-13 nuclear magnetic resonance (NMR) spectrum were recorded on a Bruker AV500 NMR spectrometer operating at a carrier frequency of 500.13 MHz, using a Bruker 4 mm H/F/X BB triple resonance CPMAS probe. The spectrum was collected utilizing proton/carbon-13 variable-amplitude cross-polarization (VACP) at 80 kHz, with a contact time of 3 ms. Other experimental parameters used for data acquisition were a proton 90-degree pulse of 100 kHz, TPPM decoupling at 100 kHz, a pulse delay of 13.5 s, and signal averaging for 5160 scans. The magic-angle spinning (MAS) rate was set to 13 kHz. A Lorentzian line broadening of 50 Hz was applied to the spectrum before Fourier Transformation. Chemical shifts are reported on the TMS scale using the carbonyl carbon of glycine (176.70 ppm.) as a secondary reference.

Example 1

Preparation of Compound A

Compound A was prepared using methods described in U.S. Patent Publication No. US20120083483.

Example 2

Preparation of Compound A/Stearic Acid Inclusion Complex

Method 1

To a scintillation vial was added Compound A (0.902 g) and stearic acid (0.0984 g), followed by water (10 mL). The resulting solution was heated to 60° C. and allowed to age at this temperature for about 15 hours. The resulting mixture was then filtered to provide a crystalline Compound A/stearic acid Inclusion Complex.

Method 2

To an amber bottle was added a co-amorphous Compound A/stearic acid complex obtained by hot melt extrusion (with an initial composition of 89 weight % Compound A and 11 weight % stearic acid). The co-amorphous material was thermally annealed in a vacuum oven under reduced pressure at 115° C. to provide a crystalline solid which was ground using a mortar and pestle to provide a Compound A/stearic acid Inclusion Complex as a powder.

Analytical Chemistry Data:

| Composition, wt % | | |
| --- | --- | --- |
| Compound A | Stearic Acid | KF |
| 88.26 | 10.0 | 0.13 |

Characteristic carbon-13 isotropic chemical shifts for the Compound A/stearic acid Inclusion Complex were measured and observed at 15.54, 20.31, 21.7023, 22.48, 26.14, 27.20, 29.29, 30.62, 31.16, 34.03, 37.18, 49.36, 50.11, 63.25, 68.68, 69.92, 72.27, 77.27, 78.15, 80.52, 92.65, 93.52, 102.11, 103.90, 120.00, 120.60, 123.83, 125.12, 129.69, 133.82, 141.59, 150.42, 151.15, 152.16, 167.04, 174.15, 181.94, and 183.46 ppm.

A DSC Thermogram of the Compound A/stearic acid Inclusion Complex was obtained and showed a broad endotherm with extrapolated onset ($T_{onset}$) at 129.9° C.

$T_{peak}$=132.0° C.; and ΔH=79.2 J/g was observed that was consistent with a melting transition.

An XRPD pattern of the Compound A/stearic acid Inclusion Complex was obtained and 2Θ values and the corresponding d-spacings include the following:

| 2-Θ, ° | d-spacing, Å | Relative Intensity, % |
|---|---|---|
| 6.57 | 13.46 | 100 |
| 6.90 | 12.82 | 88 |
| 8.25 | 10.72 | 38 |
| 8.72 | 10.14 | 12 |
| 8.95 | 9.88 | 16 |
| 10.58 | 8.36 | 21 |
| 11.43 | 7.74 | 15 |
| 11.73 | 7.54 | 26 |
| 12.43 | 7.12 | 5 |
| 12.74 | 6.95 | 10 |
| 12.90 | 6.86 | 7 |
| 13.17 | 6.72 | 12 |
| 13.67 | 6.48 | 29 |
| 14.40 | 6.15 | 4 |
| 15.01 | 5.90 | 16 |
| 15.59 | 5.69 | 36 |
| 16.18 | 5.48 | 4 |
| 16.58 | 5.35 | 13 |
| 16.77 | 5.29 | 10 |
| 17.42 | 5.09 | 9 |
| 17.70 | 5.01 | 22 |
| 17.90 | 4.96 | 66 |
| 18.18 | 4.88 | 8 |
| 18.40 | 4.82 | 21 |
| 18.86 | 4.71 | 17 |
| 19.10 | 4.65 | 43 |
| 19.60 | 4.53 | 7 |
| 20.00 | 4.44 | 6 |
| 20.50 | 4.33 | 14 |
| 20.71 | 4.29 | 14 |
| 20.98 | 4.23 | 30 |
| 21.21 | 4.19 | 14 |
| 21.50 | 4.13 | 5 |
| 21.77 | 4.08 | 4 |
| 22.30 | 3.99 | 8 |
| 22.50 | 3.95 | 7 |
| 22.76 | 3.91 | 5 |
| 23.04 | 3.86 | 7 |
| 23.48 | 3.79 | 26 |
| 23.69 | 3.76 | 10 |
| 23.95 | 3.72 | 7 |
| 24.45 | 3.64 | 10 |
| 24.66 | 3.61 | 14 |
| 24.94 | 3.57 | 23 |
| 25.41 | 3.51 | 3 |
| 25.60 | 3.48 | 3 |
| 26.09 | 3.42 | 6 |
| 26.45 | 3.37 | 7 |
| 26.62 | 3.35 | 10 |
| 26.83 | 3.32 | 11 |
| 27.48 | 3.25 | 3 |
| 28.15 | 3.17 | 2 |
| 28.49 | 3.13 | 2 |
| 28.88 | 3.09 | 7 |
| 29.14 | 3.07 | 7 |
| 29.46 | 3.03 | 10 |
| 29.88 | 2.99 | 7 |
| 30.64 | 2.92 | 3 |
| 30.89 | 2.89 | 7 |
| 31.94 | 2.80 | 3 |
| 32.47 | 2.76 | 2 |
| 33.96 | 2.64 | 2 |
| 35.39 | 2.54 | 2 |
| 35.81 | 2.51 | 2 |
| 37.46 | 2.40 | 2 |
| 39.31 | 2.29 | 3 |

Example 3

Preparation of Compound A/Palmitic Acid Inclusion Complex

To a 400 mL reactor, was added Compound A (40.0 g) and palmitic acid (4.41 g), followed by water (400 mL, 10 volumes). The resulting solution was heated to 65° C. and allowed to age at this temperature for five days. The resulting mixture was then filtered to provide a crystalline Compound A/Palmitic Acid Inclusion Complex.

Analytical Chemistry Data:

| Composition, wt % | | |
|---|---|---|
| Compound A | Palmitic Acid | KF |
| 91.49 | 9.97 | 0.11 |

Characteristic carbon-13 isotropic chemical shifts for the Compound A/palmitic acid Inclusion Complex were measured and observed at 14.85, 21.74, 22.56, 26.04, 29.14, 30.63, 31.14, 32.43, 33.56, 37.07, 49.41, 49.99, 62.99, 68.62, 69.78, 72.29, 77.00, 78.20, 80.53, 93.56, 102.11, 103.87, 119.96, 120.78, 123.72, 125.13, 129.78, 133.94, 141.64, 150.46, 151.22, 152.12, 167.11, 173.97, 181.75, and 183.24 ppm.

A DSC Thermogram of the Compound A/palmitic acid Inclusion Complex was obtained and showed a broad endotherm with extrapolated onset ($T_{onset}$) at 129.6° C. $T_{peak}$=131.2° C.; and ΔH=73.5 J/g was observed that was consistent with a melting transition.

An XRPD pattern of the Compound A/palmitic acid Inclusion Complex was obtained and 2Θ values and the corresponding d-spacings include the following:

| 2-Θ, ° | d-spacing, Å | Relative Intensity, % |
|---|---|---|
| 6.57 | 13.46 | 100 |
| 6.87 | 12.86 | 90 |
| 8.25 | 10.72 | 32 |
| 8.71 | 10.15 | 14 |
| 8.95 | 9.88 | 15 |
| 10.58 | 8.36 | 26 |
| 11.44 | 7.73 | 17 |
| 11.66 | 7.59 | 26 |
| 12.47 | 7.10 | 6 |
| 12.78 | 6.93 | 11 |
| 13.12 | 6.75 | 13 |
| 13.66 | 6.48 | 35 |
| 14.39 | 6.15 | 5 |
| 15.02 | 5.90 | 20 |
| 15.61 | 5.68 | 58 |
| 16.19 | 5.48 | 5 |
| 16.58 | 5.35 | 18 |
| 16.79 | 5.28 | 12 |
| 17.40 | 5.10 | 15 |
| 17.76 | 4.99 | 60 |
| 17.93 | 4.95 | 93 |
| 18.43 | 4.82 | 40 |
| 19.16 | 4.63 | 85 |
| 19.62 | 4.52 | 10 |
| 20.05 | 4.43 | 10 |
| 20.60 | 4.31 | 32 |
| 21.03 | 4.23 | 49 |
| 21.26 | 4.18 | 27 |
| 21.78 | 4.08 | 7 |
| 22.33 | 3.98 | 17 |
| 22.41 | 3.97 | 18 |
| 22.84 | 3.89 | 8 |
| 23.06 | 3.85 | 11 |

-continued

| 2-Θ, ° | d-spacing, Å | Relative Intensity, % |
|---|---|---|
| 23.54 | 3.78 | 54 |
| 24.00 | 3.71 | 18 |
| 24.57 | 3.62 | 34 |
| 25.00 | 3.56 | 42 |
| 25.57 | 3.48 | 6 |
| 26.11 | 3.41 | 14 |
| 26.48 | 3.36 | 18 |
| 26.74 | 3.33 | 25 |
| 26.85 | 3.33 | 23 |
| 27.54 | 3.24 | 6 |
| 28.17 | 3.17 | 5 |
| 28.58 | 3.12 | 7 |
| 28.96 | 3.08 | 13 |
| 29.20 | 3.06 | 12 |
| 29.57 | 3.02 | 29 |
| 29.84 | 2.99 | 19 |
| 30.68 | 2.91 | 5 |
| 30.96 | 2.89 | 12 |
| 31.99 | 2.80 | 6 |
| 32.44 | 2.76 | 4 |
| 33.53 | 2.67 | 4 |
| 33.94 | 2.64 | 7 |
| 34.92 | 2.57 | 4 |
| 35.39 | 2.53 | 5 |
| 35.90 | 2.50 | 6 |
| 37.38 | 2.40 | 6 |
| 38.82 | 2.32 | 4 |
| 39.40 | 2.29 | 7 |

Example 4

Preparation of Compound A Palmitic Acid/Stearic Acid Inclusion Complex

To a scintillation vial was added a blend of Compound A/palmitic acid inclusion complex (1.673 g, made using the method described in Example 3 above) and magnesium stearate (0.1855 g), followed by water (10 mL). The resulting solution was heated to 65° C. and allowed to age at this temperature for four days. The resulting mixture was then filtered to provide a crystalline Compound A/palmitic acid/stearic acid Inclusion Complex.

Analytical Chemistry Data:

| Composition, wt % | | | |
|---|---|---|---|
| Compound A | Stearic Acid | Palmitic Acid | KF |
| 88.30 | 5.19 | 5.79 | 0.10 |

Characteristic carbon-13 isotropic chemical shifts for the Compound A/stearic acid/palmitic acid inclusion complex were measured and observed at 14.98, 20.45, 21.78, 22.49, 26.13, 29.29, 30.65, 31.15, 32.52, 33.58, 37.11, 49.38, 50.05, 63.14, 68.63, 69.85, 72.28, 77.09, 78.20, 80.54, 93.53, 102.12, 103.88, 119.99, 120.76, 123.84, 125.15, 129.75, 133.85, 141.59, 150.46, 151.20, 152.16, 167.08, 174.05, 181.86, and 183.36 ppm.

A DSC Thermogram of Compound A/palmitic acid/stearic acid Inclusion Complex was obtained and showed a broad endotherm with extrapolated onset ($T_{onset}$) at 129.6° C.; $T_{peak}$=131.0° C.; and ΔH=72.4 J/g was observed that was consistent with a melting transition.

An XRPD pattern of the Inclusion Complex was obtained. 2Θ values and the corresponding d-spacings include the following:

| 2-Θ, ° | d-spacing, Å | Relative Intensity, % |
|---|---|---|
| 6.55 | 13.49 | 63 |
| 6.87 | 12.87 | 55 |
| 8.24 | 10.73 | 28 |
| 8.73 | 10.13 | 11 |
| 8.95 | 9.88 | 14 |
| 10.57 | 8.37 | 25 |
| 11.48 | 7.71 | 17 |
| 11.72 | 7.55 | 33 |
| 12.45 | 7.11 | 6 |
| 12.79 | 6.92 | 13 |
| 13.14 | 6.74 | 17 |
| 13.25 | 6.68 | 12 |
| 13.68 | 6.47 | 37 |
| 14.42 | 6.14 | 8 |
| 15.04 | 5.89 | 23 |
| 15.62 | 5.67 | 59 |
| 16.21 | 5.47 | 7 |
| 16.59 | 5.34 | 21 |
| 16.81 | 5.27 | 14 |
| 17.42 | 5.09 | 15 |
| 17.77 | 4.99 | 54 |
| 17.94 | 4.94 | 100 |
| 18.44 | 4.81 | 39 |
| 18.91 | 4.69 | 26 |
| 19.17 | 4.63 | 89 |
| 19.65 | 4.52 | 11 |
| 20.05 | 4.43 | 11 |
| 20.60 | 4.31 | 32 |
| 21.05 | 4.22 | 52 |
| 21.22 | 4.19 | 29 |
| 21.54 | 4.13 | 11 |
| 21.81 | 4.07 | 9 |
| 22.38 | 3.97 | 19 |
| 22.84 | 3.89 | 11 |
| 23.06 | 3.86 | 12 |
| 23.54 | 3.78 | 51 |
| 23.99 | 3.71 | 18 |
| 24.56 | 3.62 | 31 |
| 25.00 | 3.56 | 38 |
| 25.45 | 3.50 | 8 |
| 25.66 | 3.47 | 8 |
| 26.11 | 3.41 | 13 |
| 26.52 | 3.36 | 20 |
| 26.70 | 3.34 | 24 |
| 26.86 | 3.32 | 21 |
| 27.11 | 3.29 | 8 |
| 27.54 | 3.24 | 8 |
| 28.17 | 3.17 | 6 |
| 28.59 | 3.12 | 9 |
| 28.97 | 3.08 | 16 |
| 29.21 | 3.06 | 15 |
| 29.57 | 3.02 | 29 |
| 29.83 | 2.99 | 20 |
| 30.68 | 2.91 | 8 |
| 30.96 | 2.89 | 13 |
| 31.41 | 2.85 | 4 |
| 31.99 | 2.80 | 9 |
| 32.47 | 2.76 | 7 |
| 32.90 | 2.72 | 4 |
| 33.49 | 2.68 | 6 |
| 33.92 | 2.64 | 9 |
| 34.92 | 2.57 | 6 |
| 35.38 | 2.54 | 8 |
| 35.88 | 2.50 | 7 |
| 37.34 | 2.41 | 8 |
| 38.85 | 2.32 | 6 |
| 39.38 | 2.29 | 9 |

What is claimed is:

1. An inclusion complex comprising (a) the compound having the structure:

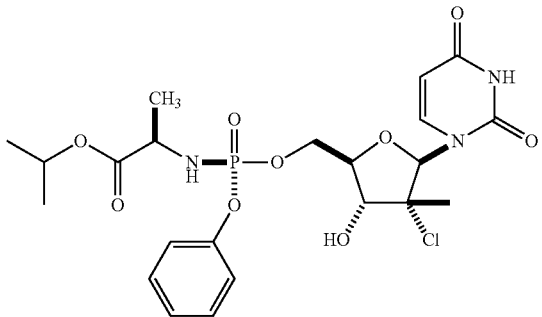

or a pharmaceutically acceptable salt thereof, and (b) at least one long-chain fatty acid.

2. The inclusion complex of claim 1, wherein the long-chain fatty acid is palmitic acid.

3. The inclusion complex of claim 1, wherein long-chain fatty acid is stearic acid.

4. The inclusion complex of claim 1, wherein long-chain fatty acid is a mixture of palmitic acid and stearic acid.

5. The inclusion complex of claim 2, having a stoichiometry of (a) to (b) of about 1:1.

6. The inclusion complex of claim 3, having a stoichiometry of (a) to (b) of about 1:1.

7. The inclusion complex of claim 2, which is characterized by an X-ray powder diffraction pattern comprising diffraction peaks at 2-theta values, when measured using Cu $K_\alpha$ radiation, of about 6.57, 6,87, 17.93, and 21.03 degrees.

8. The inclusion complex of claim 3, which is characterized by an X-ray powder diffraction pattern comprising diffraction peaks at 2-theta values, when measured using Cu $K_\alpha$ radiation, of about 6.57, 6.90, 17.90, and 20.98 degrees.

9. The inclusion complex of claim 4, which is characterized by an X-ray powder diffraction pattern comprising diffraction peaks at 2-theta values, when measured using Cu $K_\alpha$ radiation, of about 6.55, 15.62, 17.94, and 19.17 degrees.

10. The inclusion complex of claim 2, which is characterized by a DSC thermogram having an endothermic transition at about 132 degrees centrigrade.

11. The inclusion complex of claim 3, which is characterized by a DSC thermogram having an endothermic transition at about 131 degrees centrigrade.

12. The inclusion complex of claim 4, which is characterized by a DSC thermogram having an endothermic transition at about 131 degrees centrigrade.

13. The inclusion complex of claim 2, which is characterized by a solid state carbon-13 NMR spectrum having isotropic chemical shifts at 14.85, 21.74, 22.56, 26.04, 29.14, 30.63, 31.14, 32.43, 33.56, 37.07, 49.41, 49.99, 62.99, 68.62, 69.78, 72.29, 77.00, 78.20, 80.53, 93.56, 102.11, 103.87, 119.96, 120.78, 123.72, 125.13, 129.78, 133.94, 141.64, 150.46, 151.22, 152.12, 167.11, 173.97, 181.75, and 183.24 ppm.

14. The inclusion complex of claim 3, which is characterized by a solid state carbon-13 NMR spectrum having isotropic chemical shifts at 15.54, 20.31, 21.7023, 22.48, 26.14, 27.20, 29.29, 30.62, 31.16, 34.03, 37.18, 49.36, 50.11, 63.25, 68.68, 69.92, 72.27, 77.27, 78.15, 80.52, 92.65, 93.52, 102.11, 103.90, 120.00, 120.60, 123.83, 125.12, 129.69, 133.82, 141.59, 150.42, 151.15, 152.16, 167.04, 174.15, 181.94, and 183.46 ppm.

15. The inclusion complex of claim 4, which is characterized by a solid state carbon-13 NMR spectrum having isotropic chemical shifts at 14.98, 20.45, 21.78, 22.49, 26.13, 29.29, 30.65, 31.15, 32.52, 33.58, 37.11, 49.38, 50.05, 63.14, 68.63, 69.85, 72.28, 77.09, 78.20, 80.54, 93.53, 102.12, 103.88, 119.99, 120.76, 123.84, 125.15, 129.75, 133.85, 141.59, 150.46, 151.20, 152.16, 167.08, 174.05, 181.86, and 183.36 ppm.

16. A pharmaceutical composition comprising the inclusion complex of claim 1, and one or more pharmaceutically acceptable excipients.

17. A method for treating HCV in a patient, said method comprising administering to said patient the inclusion complex of claim 1.

* * * * *